US011092379B2

(12) United States Patent
Schumaier et al.

(10) Patent No.: US 11,092,379 B2
(45) Date of Patent: Aug. 17, 2021

(54) DRYER AND SANITIZER FOR RECHARGEABLE ELECTRONIC DEVICES

(71) Applicant: Ear Technology Corporation, Johnson City, TN (US)

(72) Inventors: Daniel R. Schumaier, Elizabethton, TN (US); Karlee Harrison, Johnson City, TN (US)

(73) Assignee: Ear Technology Corporation, Johnson City, TN (US)

( * ) Notice: Subject to any disclaimer, the term of this patent is extended or adjusted under 35 U.S.C. 154(b) by 53 days.

(21) Appl. No.: 16/665,045

(22) Filed: Oct. 28, 2019

(65) Prior Publication Data
US 2021/0041166 A1    Feb. 11, 2021

Related U.S. Application Data

(60) Provisional application No. 62/883,761, filed on Aug. 7, 2019.

(51) Int. Cl.
*H04R 25/00*    (2006.01)
*F26B 3/04*    (2006.01)
*A61L 2/00*    (2006.01)

(52) U.S. Cl.
CPC .............. *F26B 3/04* (2013.01); *A61L 2/0023* (2013.01); *H04R 25/00* (2013.01); *F26B 2200/00* (2013.01); *H04R 2225/31* (2013.01); *H04R 2460/17* (2013.01)

(58) Field of Classification Search
CPC ...... A61L 2/0023; F26B 3/04; F26B 2200/00; H04R 25/00; H04R 2460/17; H04R 2225/31
See application file for complete search history.

(56) References Cited

U.S. PATENT DOCUMENTS

| 5,404,105 A | 4/1995 | Chari |
| 5,640,783 A | 6/1997 | Schumaier |
| 5,852,879 A | 12/1998 | Schumaier |

(Continued)

FOREIGN PATENT DOCUMENTS

| CN | 201018665 | 2/2008 |
| CN | 103747388 A | 4/2014 |

(Continued)

OTHER PUBLICATIONS

Extended European Search Report for EP 20188577.9, dated Nov. 26, 2020, 8 pages.

(Continued)

*Primary Examiner* — Brian Ensey
(74) *Attorney, Agent, or Firm* — Luedeka Neely Group, P.C.

(57) ABSTRACT

A dryer and sanitizer unit for rechargeable electronic devices, including a drying chamber formed by a base and a repositionable lid that covers the base, the drying chamber configured to enclose one or more rechargeable electronic devices and one or more electronic charger units associated with the one or more electronic devices, the drying chamber including one or more passages through which electric cords associated with the one or more electronic charger units may pass out of the drying chamber; and one or more disinfecting light sources located within the drying chamber.

22 Claims, 7 Drawing Sheets

(56) References Cited

U.S. PATENT DOCUMENTS

| | | | |
|---|---|---|---|
| D414,304 S | 9/1999 | Schumaier | |
| 6,399,920 B1 | 6/2002 | Guinn | |
| D467,394 S | 12/2002 | Schumaier | |
| 6,625,900 B1 | 9/2003 | Tobias | |
| 7,062,057 B2 | 6/2006 | Wu | |
| D536,491 S | 2/2007 | Schumaier | |
| 7,182,820 B2 | 2/2007 | Campbell et al. | |
| 8,112,900 B2 * | 2/2012 | Romanek | F26B 9/003 34/202 |
| 8,689,461 B1 | 4/2014 | Cookson et al. | |
| 9,709,327 B2 * | 7/2017 | Marchiori | F26B 5/12 |
| 9,839,707 B2 | 12/2017 | Won | |
| 9,843,870 B2 | 12/2017 | Naumann | |
| 2003/0196687 A1 | 10/2003 | Campbell et al. | |
| 2004/0073275 A1 | 4/2004 | Maltan et al. | |
| 2004/0118427 A1 | 6/2004 | Palfy et al. | |
| 2006/0220620 A1 | 10/2006 | Aradachi et al. | |
| 2008/0175761 A1 | 7/2008 | Thur et al. | |
| 2009/0080679 A1 | 3/2009 | Rass | |
| 2009/0296968 A1 | 12/2009 | Wu et al. | |
| 2010/0011613 A1 | 1/2010 | Husung | |
| 2010/0088916 A1 | 4/2010 | Romanek | |
| 2010/0088922 A1 | 4/2010 | Romanek | |
| 2012/0006995 A1 | 1/2012 | Greuel | |
| 2012/0216418 A1 | 8/2012 | Serman et al. | |
| 2013/0004367 A1 | 1/2013 | Roberts | |
| 2013/0330235 A1 | 12/2013 | Stibich et al. | |
| 2015/0162770 A1 | 6/2015 | Choi et al. | |
| 2015/0250646 A1 | 9/2015 | Lipford et al. | |
| 2016/0008498 A1 | 1/2016 | Boysset et al. | |
| 2016/0101202 A1 | 4/2016 | Gil et al. | |
| 2016/0165367 A1 | 6/2016 | Ochsenbein | |
| 2016/0277848 A1 | 9/2016 | Naumann | |
| 2016/0301287 A1 | 10/2016 | Nagata et al. | |
| 2016/0302567 A1 | 10/2016 | Gorelick | |
| 2018/0123355 A1 | 5/2018 | Olson et al. | |
| 2018/0123367 A1 | 5/2018 | Higgins et al. | |
| 2019/0167827 A1 | 6/2019 | Gaska et al. | |
| 2019/0208342 A1 | 7/2019 | Higgins et al. | |
| 2019/0297437 A1 | 9/2019 | Gil | |
| 2020/0267483 A1 | 8/2020 | Schumaier | |

FOREIGN PATENT DOCUMENTS

| | | |
|---|---|---|
| CN | 104534822 A | 4/2015 |
| CN | 205457846 U | 8/2016 |
| CN | 205901402 U | 1/2017 |
| CN | 208770000 U | 4/2019 |
| DE | 202017107151 U1 | 1/2018 |
| KR | 20120085980 A | 8/2012 |
| WO | 9848855 A1 | 11/1998 |
| WO | 2007066908 A1 | 6/2007 |

OTHER PUBLICATIONS

Ear Technology Corporation, Dry & Store Global Operation, Oct. 2005, pp. 1-7. (Year: 2005).

* cited by examiner

DRYER AND SANITIZER FOR RECHARGEABLE ELECTRONIC DEVICES

CROSS REFERENCE TO RELATED APPLICATION

This application claims priority to U.S. Provisional Application Ser. No. 62/883,761 entitled DRYER AND SANITIZER FOR RECHARGEABLE ELECTRONIC DEVICES, filed Aug. 7, 2019, incorporated by reference herein in its entirety.

FIELD

This disclosure relates to devices for drying and sanitizing electronic devices. More particularly, this disclosure relates to a dryer and sanitizer unit configured for drying and sanitizing a wide variety of rechargeable hearing instruments and their chargers which come in many different sizes and shapes from different manufacturers.

BACKGROUND

Improvement is desired in devices for charging, drying and sanitizing electronic devices. During use, the batteries of hearing aids discharge and the hearing aids collect bacteria and gather moisture.

What is desired is a convenient way to recharge hearing aids while also sanitizing and drying the hearing aids at the same time.

The present disclosure advantageously provides an easy-to-use unit that enables the charging of hearing aids while the hearing aids are sanitized and dried.

SUMMARY

The above and other needs are met by a dryer and sanitizer unit for rechargeable electronic devices.

In one aspect, a dryer and sanitizer unit according to the disclosure includes a drying chamber formed by a base and a repositionable lid that covers the base. The drying chamber is configured to enclose one or more rechargeable electronic devices and one or more electronic charger units associated with the one or more electronic devices. The drying chamber includes one or more passages through which electric cords associated with the one or more electronic charger units may pass out of the drying chamber; and one or more disinfecting light sources located within the drying chamber.

In another aspect, a dryer and sanitizer unit according to the disclosure includes a base and a lid that together define a drying chamber that encloses one or more rechargeable electronic devices and one or more charger units associated with the one or more rechargeable electronic devices.

The unit also includes one or more passages through which electric cords associated with the one or more charger units pass out of the drying chamber; one or more disinfecting light sources located within the drying chamber; a heater configured to provide heated dry air; a fan configured to circulate the heated dry air in the drying chamber; a thermostat configured to measure air temperature in the drying chamber; and a controller in electrical communication with the thermostat and the heater drying for maintaining the air temperature in the drying chamber above a predetermined drying temperature and below a predetermined upper temperature corresponding to a temperature above which rechargeable batteries associated with the rechargeable electronic devices are vulnerable to overheating.

In a further aspect, a dryer and sanitizer unit according to the disclosure includes a base and a lid that together define a drying chamber that is configured to enclose one or more rechargeable electronic devices locatable within the drying chamber; one or more disinfecting light sources located within the drying chamber; a heater configured to provide heated dry air; a fan configured to circulate the heated dry air in the drying chamber; a thermostat configured to measure air temperature in the drying chamber; and a controller in electrical communication with the thermostat and the heater drying for maintaining the air temperature in the drying chamber above a predetermined drying temperature and below a predetermined upper temperature corresponding to a temperature above which rechargeable batteries associated with the rechargeable electronic devices are vulnerable to overheating.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
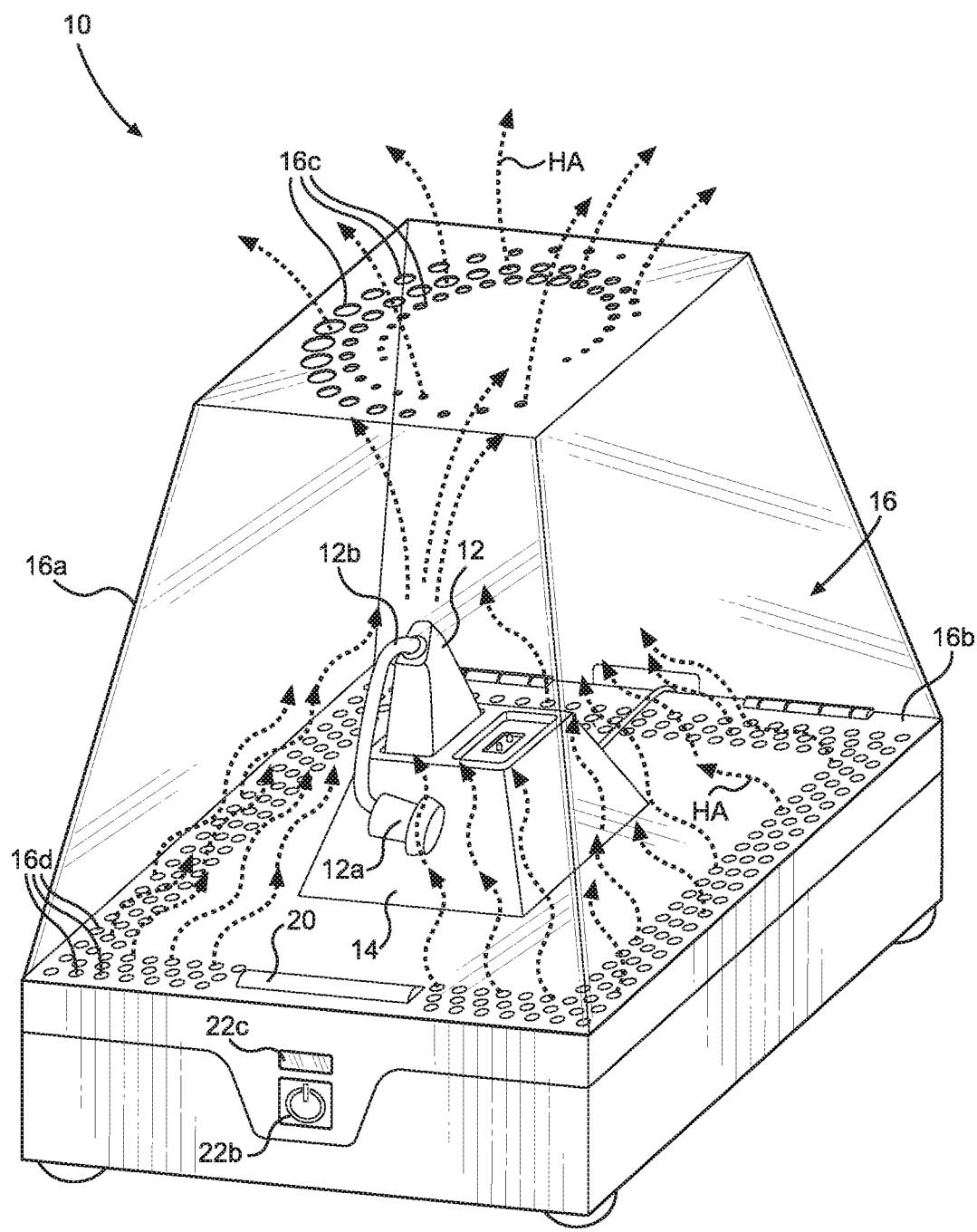
FIG. 1 is a perspective view of an embodiment of a dryer and sanitizing unit according to the disclosure as used to dry and sanitize an electronic device such as a hearing aid.
Figure 2:
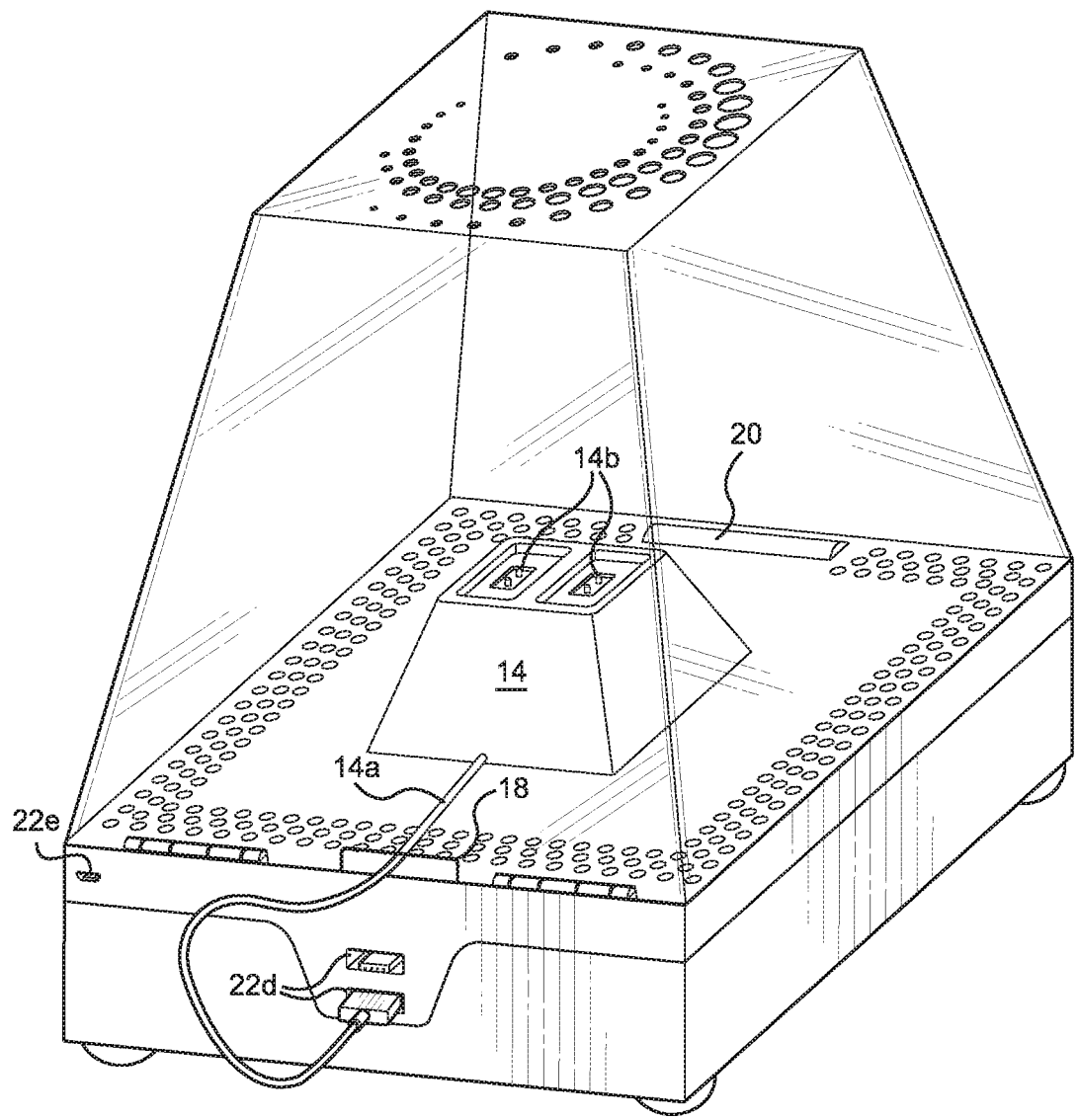
FIG. 2 shows the dryer and sanitizing unit of FIG. 1 with a charger for a hearing aid installed.
Figure 3:
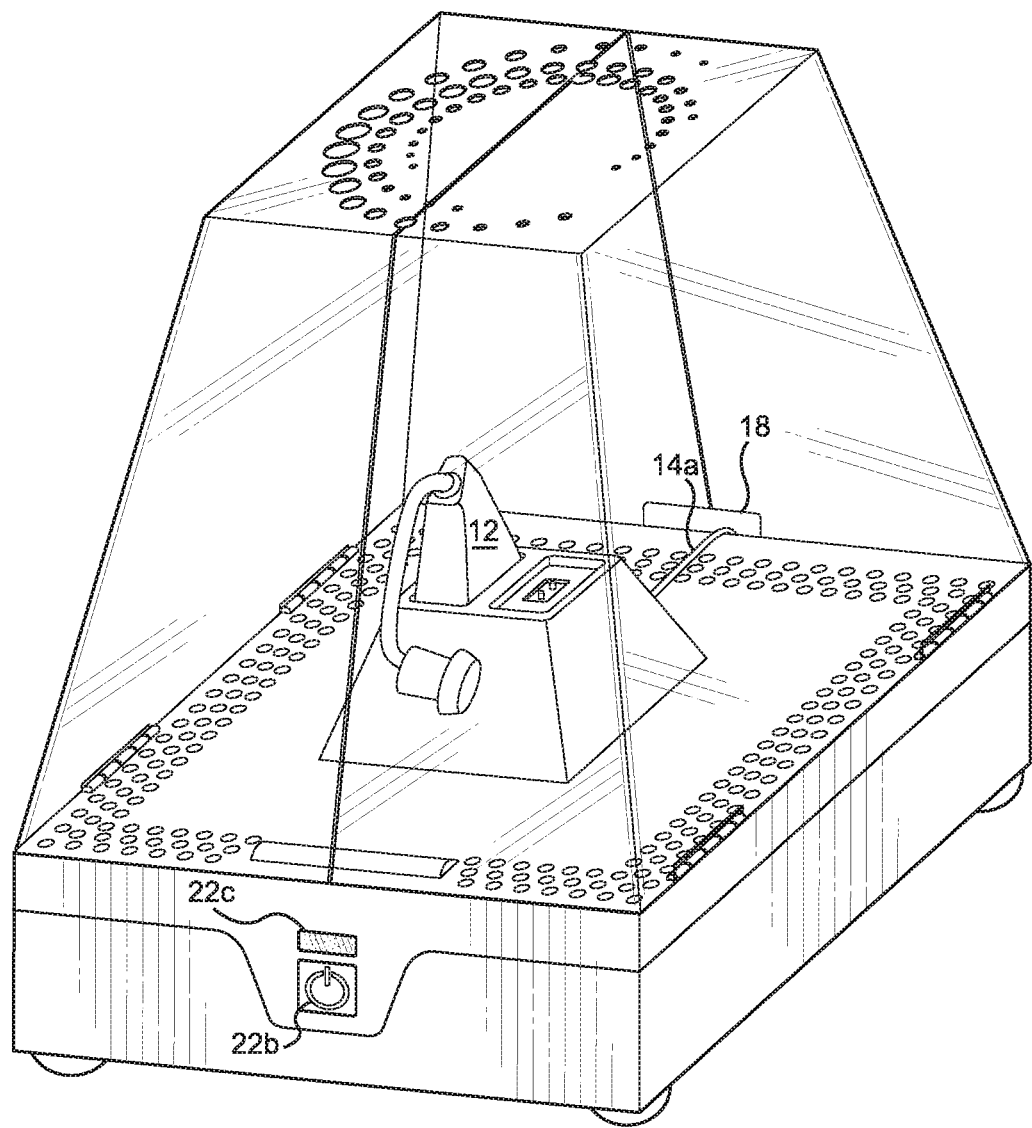
FIG. 3 shows the dryer and sanitizing unit of FIG. 1 with a charger for a hearing aid and a hearing aid installed on the charger.

With initial reference to FIGS. 1-3 there is shown a preferred embodiment of a dryer and sanitizer unit 10 according to the disclosure configured for drying and sanitizing rechargeable electronic devices, such as hearing instruments in the nature of a hearing aid 12, including tips 12*a*, and tubes 12*b* and seated in a charger 14 having an electric cord 14*a*. The hearing aid 12 may be a conventional hearing aid. The charger 14 is specific to the hearing aid 12 and includes a pair of charging receptacles 14*b* for receiving a pair of the hearing aids 12.

FIGS. 4-7 depict operation of the unit 10 to charge, dry, and sanitize rechargeable devices, such as a pair of the hearing aids 12. In overview, the unit 10 is configured to receive the hearing aids 12 on the charger 14 to enable their charging, drying and sanitization. In this regard, initially the hearing aids are disinfected as by application of sanitizing illumination. Following or simultaneous with the sanitization, heated dry air is flowed over the hearing aids to remove moisture.

The dryer and sanitizer unit 10 is configured to include a drying chamber 16 provided by a lid 16*a* over a base 16*b*.

The unit 10 also includes one or more passages 18 for passage of electric cords, such as the cord 14a, out of the drying chamber. The passages 18 are desirably located on the lid 16a but could be provided on the base 16b if desired. The unit 10 also includes one or more disinfecting light sources 20 located within the drying chamber 16. The disinfecting light sources 20 are preferably UV-C lamps such as high intensity 50 mm linear germicidal lamps operating at a wavelength of 253.7 nm and rated at 70 uW/cm$^2$.

Figure 8:
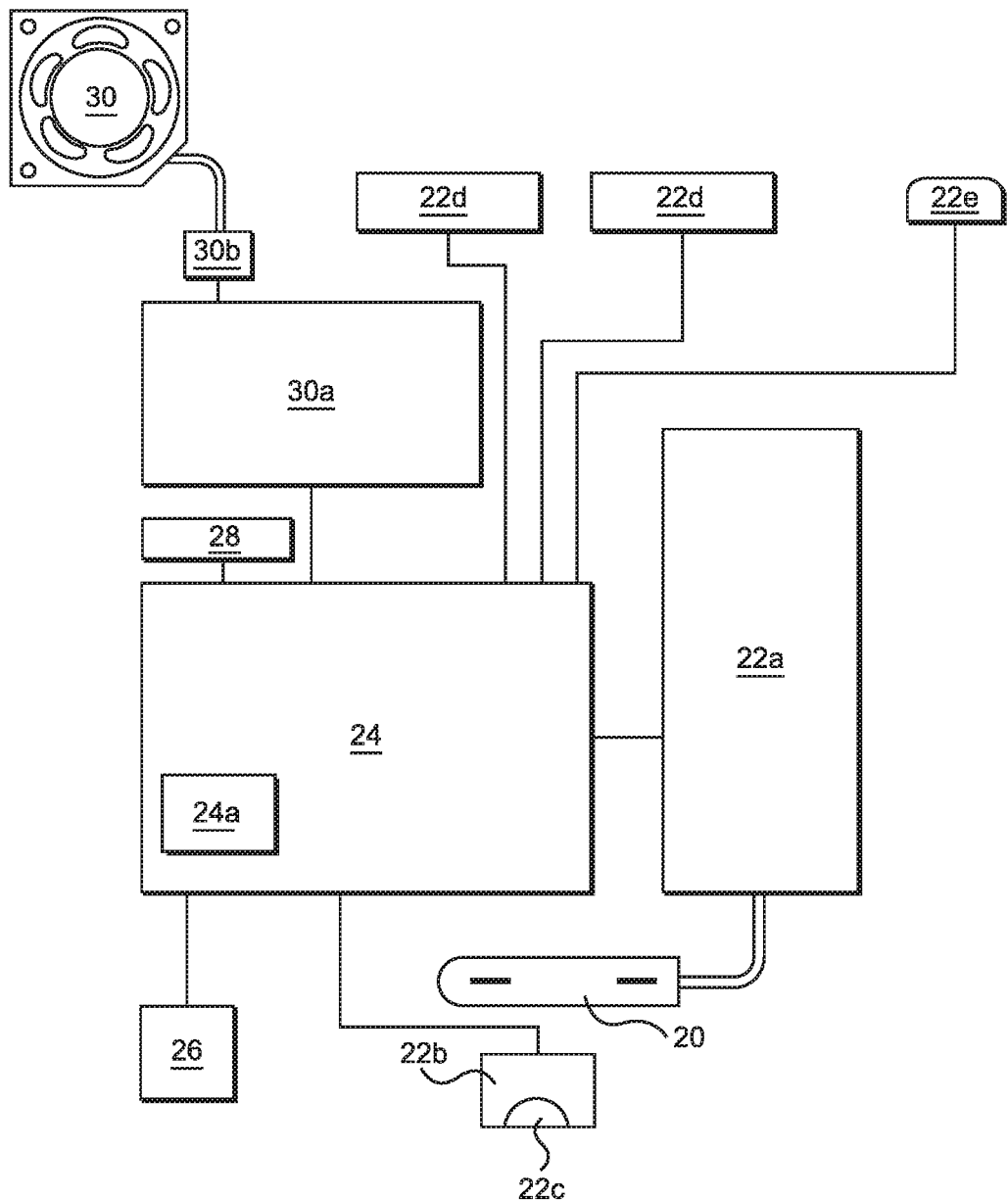
FIG. 8 shows a functional block diagram of electrical components of an embodiment of the dryer and sanitizer unit.
Figure 9:
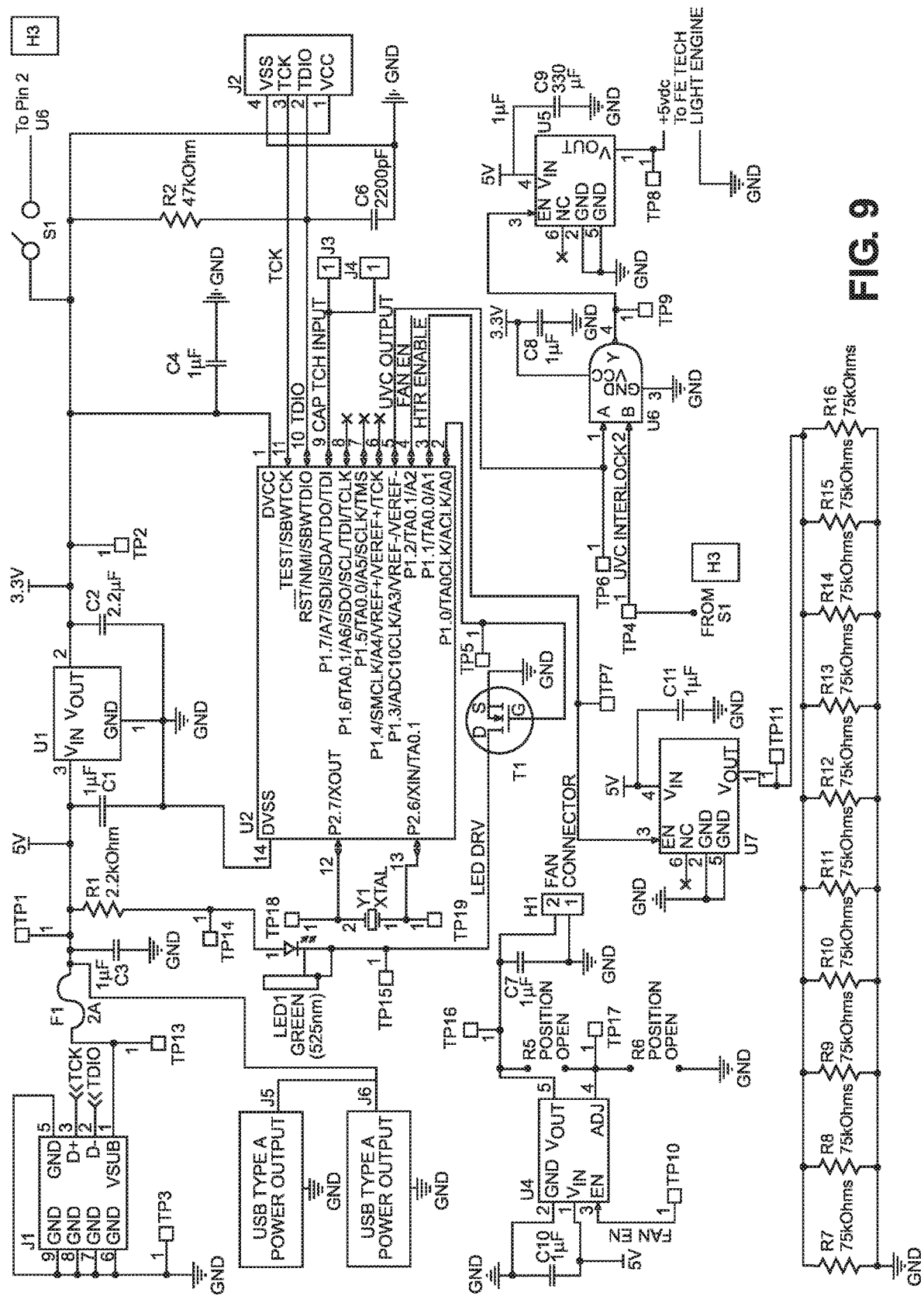
FIG. 9 shows a schematic diagram of an embodiment of an electrical circuit for use with the dryer and sanitizer unit.

With additional reference to FIG. 8, various electronic devices of an embodiment of the unit 10 are shown as located in the base 16b. The light sources 20 are preferably in electrical communication with a lamp control circuit 22a. Electrical power is controlled as by an on/off switch 22b, such as a capacitive touch switch, with an LED indicator 22c to indicate that the unit 10 is on. Electrical power may be supplied to the charger 14 by plugging the cord 14a into one or more power outlets 22d to which power is supplied by a microprocessor 24. The unit 10 preferably receives 5-volt direct current electrical power via one or more input power connectors 22e, such as USB micro connectors.

The lamp control circuit 22a may be programmed to operate the light sources 20 for a predetermined time sufficient to provide a 4-log theoretical kill rate of 99.99%. A desired operation time of the light sources 20 is from about 1.5 to about 3 minutes or longer to achieve this level of disinfection. In this regard, the lamp control circuit 22a is also in electrical communication with a microprocessor 24. The microprocessor 24 is configured to control the operation of the light circuit 22a. To enhance the effect of the light sources 20, one or more interior surfaces of the lid 16a may be UV-reflective.

In a preferred embodiment, the microprocessor 24 is also operably associated with a lid open detection circuit 26 in communication with both the lid 16a and the light sources 20. The lid open detection circuit 26 is operable to turn off the light sources 20 if the lid 16a is opened during operation of the disinfecting light sources 20.

The lid 16a preferably has a square pyramidal shape with a flat top that includes air outlet vents 16c. The base 16b includes air inlet vents 16d through which heated dry air HA is supplied into the drying chamber 16. In one embodiment, the lid 16a is formed by two independently-hinged halves that operate like a clam shell.

The heated dry air HA is preferably supplied at a temperature that fits the specification of the manufacturer of the batteries for the hearing aids. Generally speaking, however, it has been observed that damage can occur to some rechargeable batteries for hearing aids if they are exposed to temperatures above about 113 degrees F. (45 degrees C.) for prolonged periods of time. The flow rate and flow time of the heated dry air HA is selected based on observation of parameters that provide optimal drying, and the microprocessor 24 is programmed to provide a desired air temperature, time and fan speed to provide the desired drying effect.

A heater 28 is also operably associated with the microprocessor 24. In addition, the microprocessor 24 is operably associated with a fan 30 connected to a fan circuit 30a via a fan connector 30b to introduce the heated dry air HA into the drying chamber 16 through the vents 16d and circulate the heated dry air HA in the drying chamber 16. The microprocessor 24 controls operation of the heater 28 and the fan 30 to provide a desired flow of the heated dry air HA into the drying chamber 16. The fan 30 preferably uses a magnetic bearing assembly, available from Sunon (www.sunon.com) under the name "MagLev Motor Fan" instead of ball bearing types of fan motors. This assembly allows the unit 10 to operate with less motor noise, as well as extended life, and a higher level of reliability.

The heated dry air HA may exit the drying chamber 16 via the outlet vents 16c in the lid 16a. It is believed that operation of the unit 10 in a manner to provide a desirably controlled temperature in the drying chamber 16 in combination with a desired flow of moving air function to break the surface tension bond that water molecules have on the hearing aids, with the heated dry air HA air circulating throughout the drying chamber 16 and exiting the drying chamber 16 through the outlet vents 16c serving to remove moisture from the drying chamber 16.

The microprocessor 24 includes a thermostat 24a configured for measurement of air temperature in the drying chamber 16. The microprocessor 24 is programmed to maintain the air temperature in the drying chamber 16, that is the temperature of the heated dry air HA, above a predetermined drying temperature and below a predetermined upper temperature corresponding to a temperature above which damage would occur to rechargeable batteries of the electronic devices, such as the hearing aids 12, in the drying chamber 16.

The microprocessor 24 is preferably a customizable digitally programmable microprocessor with non-volatile memory and the thermostat 24a is preferably an internal digital thermostat for controlling the temperature within the drying chamber 16 to a high level of thermal accuracy. The microprocessor 24 also controls the on/off times of the light sources 20 and then the heater 28 and the fan 30 to provide a desired treatment cycle and automatically turns off after the treatment cycle has completed or if the lid 16a has been opened. The hearing aids 12 are recharged during the treatment cycle and may be left on the charger 14 following the treatment cycle if desired. In this regard, a treatment cycle is understood to include sanitization via the light source 20 followed by drying via the heated dry air HA.

Figure 5:
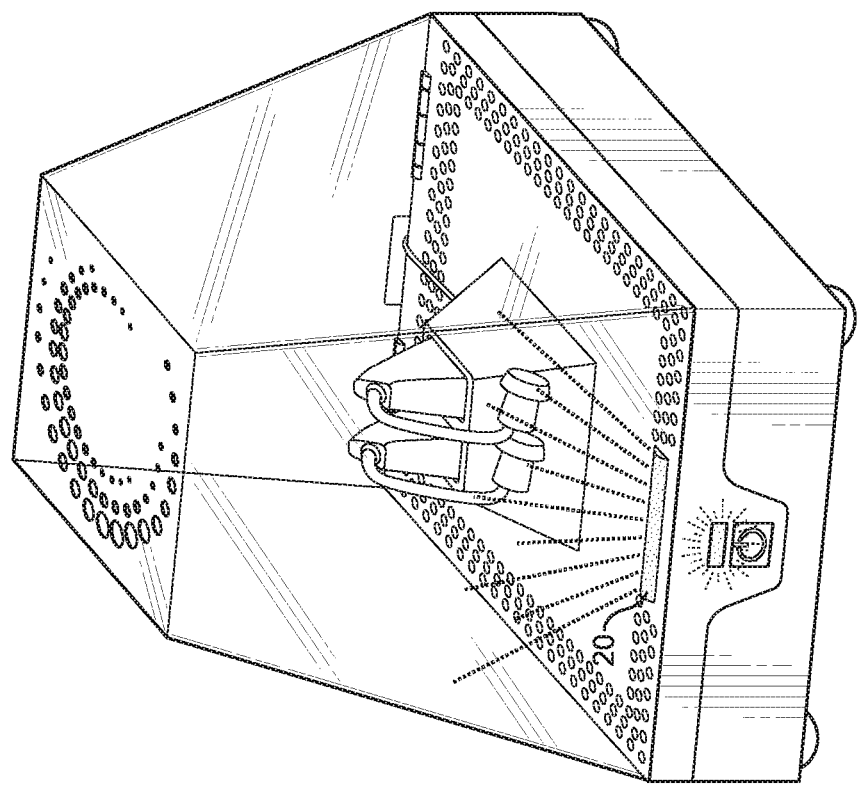
FIGS. 4-7 show use of the dryer and sanitizing unit of FIG. 1 to dry and sanitize one or more hearing aids.
Figure 4:
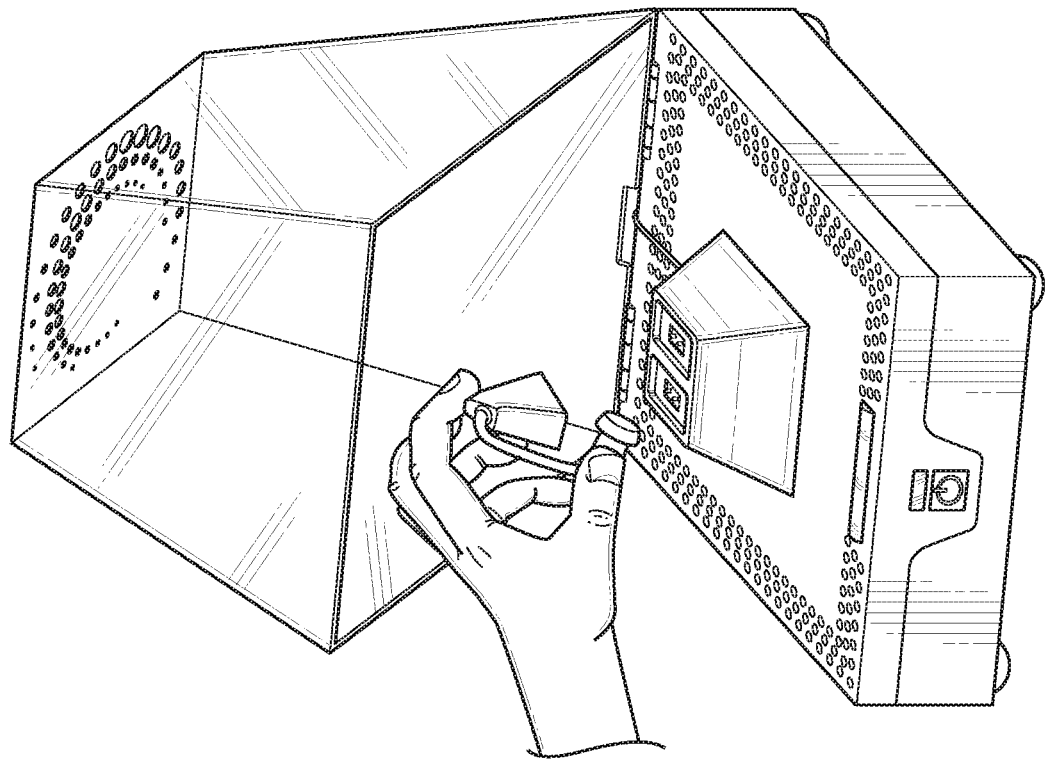

During use of the unit 10, as depicted in FIG. 4, a user may place hearing aids attached to their manufacturer-supplied charger inside the drying chamber 16, shut the lid 16a, and press the on/off switch 22b. As shown in FIG. 5, the microprocessor 24 then initiates a sanitization cycle by turning on the light sources 20, to disinfect all exposed surfaces of the hearing aids 12. After a pre-determined time has elapsed, the microprocessor 24 turns off the light sources 20 and initiates a drying cycle by turning on the heater 28, the fan 30 and the thermostat 24a.

Figure 7:
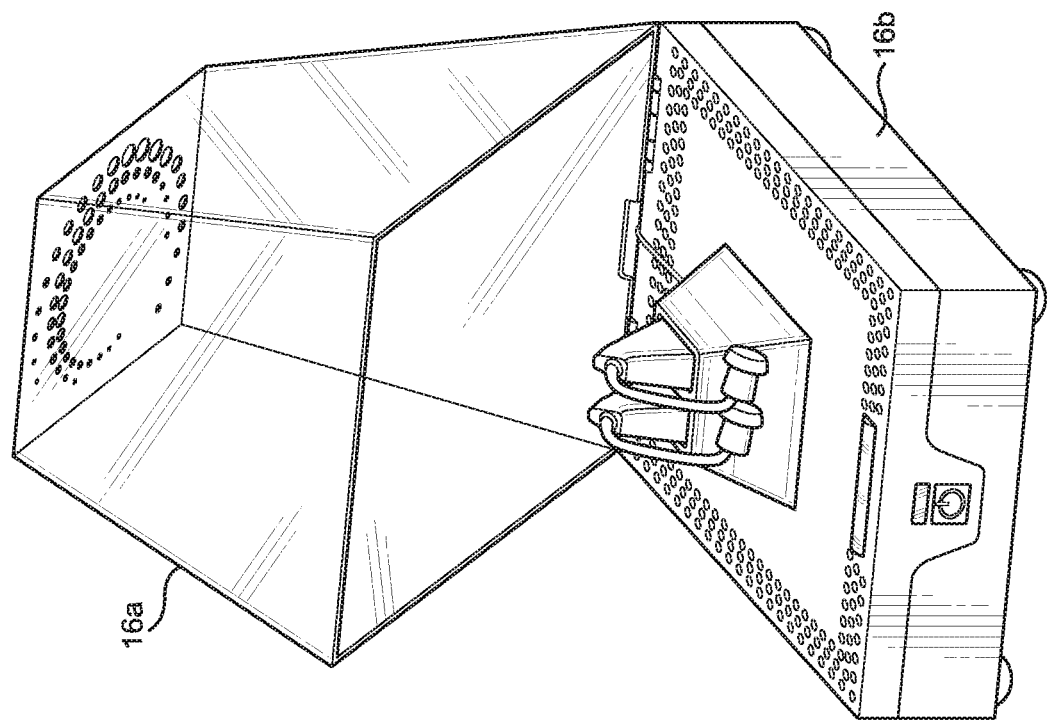
Figure 6:
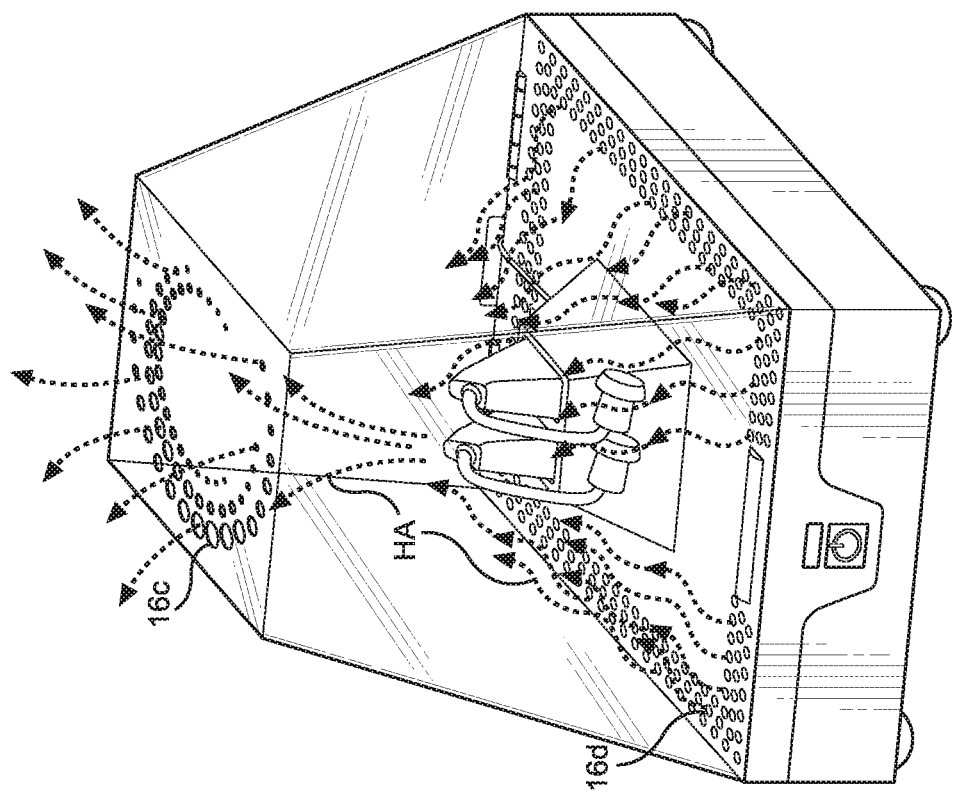

Next, as shown in FIG. 6, the heated dry air HA is introduced to the drying chamber 16 through the vents 16d of the base 16b, and circulates within the drying chamber 16, and leaves the drying chamber through the air vents 16c in the lid 16a. The circulating heated dry air HA functions to break the surface tension of water molecules on the surface of the hearing aids and draws the moisture away therefrom and out of the drying chamber 16 through the vents 16c in the lid 16a. Meanwhile, the microprocessor 24 monitors the temperature in the drying chamber using the thermostat 24a and maintains a pre-programmed temperature by controlling the output of the heater 28 and the speed of the one or more fans 30. Precise control of the temperature of the circulating air is imperative to prevent overheating of the batteries of the hearing aids and the charger. At the conclusion of the drying phase of the treatment cycle, the microprocessor 24 turns off the heater 28 and the fan 30 and the hearing aids 12 may be removed from the drying chamber 16 as shown in FIG. 7.

To accommodate electronic devices that recharge using wireless nearfield proximity charging, an embodiment of the unit 10 includes in the base an inductive coil and associated circuitry to provide the wireless nearfield proximity charging. In this embodiment, the rechargeable electronic devices may be set directly on the base above the inductive coil for charging.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

The invention claimed is:

1. A dryer and sanitizer unit for rechargeable electronic devices comprising:
   a drying chamber for enclosing one or more rechargeable electronic devices and one or more electronic charger units associated with the one or more electronic devices, the drying chamber comprising:
      a base having a substantially horizontal surface upon which the one or more rechargeable electronic devices and the one or more associated electronic charger units are placed, the base including vents in the horizontal surface through which warm air may flow into the drying chamber to contact the one or more rechargeable electronic devices, wherein the vents are disposed around a perimeter of the base to at least partially surround the one or more rechargeable electronic devices and the one or more associated electronic charger units disposed on the base;
      a repositionable lid that covers the base; and
      one or more passages through which electric cords associated with the one or more electronic charger units may pass out of the drying chamber; and
   one or more disinfecting light sources located within the drying chamber.

2. The dryer and sanitizer unit of claim 1, further comprising a thermostat operably associated with the drying chamber for measuring air temperature in the drying chamber.

3. The dryer and sanitizer unit of claim 1, wherein the rechargeable electronic devices are hearing aids.

4. The dryer and sanitizer unit of claim 1, further comprising a controller operably associated with the drying chamber for controlling air temperature in the drying chamber to maintain the air temperature in the drying chamber above a predetermined drying temperature and below a predetermined upper temperature corresponding to a temperature above which rechargeable batteries of the rechargeable electronic devices are vulnerable to overheating.

5. The dryer and sanitizer unit of claim 1, wherein the one or more disinfecting light sources are disposed in the base.

6. The dryer and sanitizer unit of claim 1, further including a fan and a heater in flow communication with the air vents in the base for introduction of a flow of warm air into the drying chamber.

7. The dryer and sanitizer unit of claim 6, further including vents located in the lid to promote the flow of warm air over the rechargeable electronic devices and provide a path for the warm air to exit the drying chamber.

8. The dryer and sanitizer unit of claim 6, wherein the disinfecting light sources are operated for a predetermined time sufficient to disinfect the rechargeable electronic devices within the drying chamber, after which the disinfecting light sources are turned off and the heater and fan are operated for a predetermined drying cycle to introduce the warm air into the drying chamber.

9. The dryer and sanitizer unit of claim 1, wherein the lid has a square pyramidal shape with a flat top that includes air vents.

10. The dryer and sanitizer unit of claim 1, wherein an interior surface of the lid is UV-reflective.

11. The dryer and sanitizer unit of claim 1, further comprising a lid open detection circuit operably associated with both the lid and the disinfecting light source and operable to turn off the disinfecting light sources if the lid is opened during operation of the disinfecting light sources.

12. The dryer and sanitizer unit of claim 1, wherein the one or more passages are disposed on the lid.

13. A dryer and sanitizer unit, comprising:
   a base and a lid that together define a drying chamber that encloses one or more rechargeable electronic devices and one or more charger units associated with the one or more rechargeable electronic devices, the base having a substantially horizontal surface upon which the one or more rechargeable electronic devices and the one or more associated electronic charger units are placed, the base including vents in the horizontal surface through which warm air may flow into the drying chamber to contact the one or more rechargeable electronic devices, wherein the vents are disposed around a perimeter of the base to at least partially surround the one or more rechargeable electronic devices and the one or more associated electronic charger units disposed on the base;
   one or more passages through which electric cords associated with the one or more charger units pass out of the drying chamber;
   one or more disinfecting light sources located within the drying chamber;
   a heater configured to provide heated dry air;
   a fan configured to circulate the heated dry air in the drying chamber;
   a thermostat configured to measure air temperature in the drying chamber; and
   a controller in electrical communication with the thermostat and the heater for maintaining the air temperature in the drying chamber above a predetermined drying temperature and below a predetermined upper temperature corresponding to a temperature above which rechargeable batteries associated with the rechargeable electronic devices are vulnerable to overheating.

14. The dryer and sanitizer unit of claim 13, further comprising vents in the lid.

15. The dryer and sanitizer unit of claim 13, wherein the disinfecting light sources are operated for a predetermined time sufficient to disinfect the electronic devices within the drying chamber, after which the disinfecting light sources are turned off and the heater and fan are operated for a predetermined drying cycle to circulate flow warm air into the drying chamber.

16. The dryer and sanitizer unit of claim 13, wherein the lid has a square pyramidal shape with a flat top that includes air vents.

17. The dryer and sanitizer unit of claim 13, wherein an interior surface of the lid is UV-reflective.

18. The dryer and sanitizer unit of claim 13, further comprising a lid open detection circuit operably associated with both the lid and the disinfecting light source and operable to turn off the disinfecting light sources if the lid is opened during operation of the disinfecting light sources.

19. The dryer and sanitizer unit of claim 13, wherein the rechargeable electronic devices are hearing aids.

20. The dryer and sanitizer unit of claim 13, wherein the lid is hinged to the base.

21. A dryer and sanitizer unit, comprising:
   a base and a lid that together define a drying chamber that is configured to enclose one or more rechargeable electronic devices locatable within the drying chamber;
   one or more disinfecting light sources located within the base of the drying chamber;
   a heater configured to provide heated dry air;
   a fan configured to circulate the heated dry air in the drying chamber;
   a thermostat configured to measure air temperature in the drying chamber; and
   a controller in electrical communication with the thermostat and the heater for maintaining the air temperature in the drying chamber above a predetermined drying temperature and below a predetermined upper temperature corresponding to a temperature above which rechargeable batteries associated with the rechargeable electronic devices are vulnerable to overheating.

22. The dryer and sanitizer unit of claim 13, wherein the one or more disinfecting light sources are disposed in the base.

\* \* \* \* \*